(12) United States Patent
Wong (10) Patent No.: US 9,668,898 B2
(45) Date of Patent: Jun. 6, 2017

(54) STENT DELIVERY SYSTEM HAVING DYNAMIC DEPLOYMENT AND METHODS OF MANUFACTURING SAME

(71) Applicant: Medtronic Vascular, Inc., Santa Rosa, CA (US)

(72) Inventor: Mark Wong, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 235 days.

(21) Appl. No.: 14/339,661

(22) Filed: Jul. 24, 2014

(65) Prior Publication Data
US 2016/0022455 A1    Jan. 28, 2016

(51) Int. Cl.
*A61F 2/958* (2013.01)
*A61F 2/915* (2013.01)
*A61M 25/10* (2013.01)
*B23P 11/00* (2006.01)
*A61F 2/88* (2006.01)

(52) U.S. Cl.
CPC .............. *A61F 2/958* (2013.01); *A61F 2/915* (2013.01); *A61M 25/10* (2013.01); *A61F 2/88* (2013.01); *A61F 2002/91516* (2013.01); *A61F 2002/91525* (2013.01); *A61F 2002/91575* (2013.01); *A61F 2002/9583* (2013.01); *A61F 2240/002* (2013.01); *A61F 2250/0018* (2013.01); *A61F 2250/0029* (2013.01); *A61F 2250/0037* (2013.01); *A61F 2250/0048* (2013.01); *B23P 11/005* (2013.01); *Y10T 29/49913* (2015.01)

(58) Field of Classification Search
CPC .. A61F 2002/91575; A61F 2002/91525; A61F 2002/91516; A61F 2250/0029; A61F 2250/0018; A61F 2250/0048; A61F 2002/9522; A61F 2/82–2002/825; A61M 25/1002–25/1004; A61B 2017/00526; B23P 11/005; Y10T 29/49908; Y10T 29/49909; Y10T 29/49913
See application file for complete search history.

(56) References Cited

U.S. PATENT DOCUMENTS

| | | |
|---|---|---|
| 5,500,180 A | 3/1996 | Anderson et al. |
| 6,063,092 A * | 5/2000 | Shin ................ A61F 2/958 |
| | | 606/108 |
| 6,210,364 B1 | 4/2001 | Anderson et al. |
| 6,283,743 B1 | 9/2001 | Traxler et al. |
| 6,283,939 B1 | 9/2001 | Anderson et al. |
| 7,597,702 B2 | 10/2009 | Eidenschink |
| 8,366,765 B2 | 2/2013 | Baldwin et al. |

(Continued)

*Primary Examiner* — Christopher Besler
*Assistant Examiner* — Matthew P Travers (57) ABSTRACT

A stent delivery system for dynamic deployment of a stent loaded thereon and a method of manufacturing the system. The stent delivery system includes a balloon catheter with a balloon in a spirally twisted delivery configuration on which a stent is crimped or otherwise loaded. The stent is made from a single, continuous strand of wire formed into a sinusoidal waveform that is wrapped into a helical pattern and joined at selected crowns. Upon inflation of the spirally twisted balloon of the stent delivery system, the stent undergoes dynamic deployment such that the stent in a deployed or expanded configuration has crowns with obtuse deployment angles and crowns with acute deployment angles.

20 Claims, 7 Drawing Sheets

(56) References Cited

U.S. PATENT DOCUMENTS

| | | | |
|---|---|---|---|
| 2005/0203605 A1* | 9/2005 | Dolan | A61F 2/2418 |
| | | | 623/1.11 |
| 2006/0134357 A1 | 6/2006 | Godaire et al. | |
| 2007/0129786 A1* | 6/2007 | Beach | A61F 2/91 |
| | | | 623/1.15 |
| 2013/0025339 A1 | 1/2013 | Costa et al. | |
| 2013/0261545 A1 | 10/2013 | Osypka | |

* cited by examiner

STENT DELIVERY SYSTEM HAVING DYNAMIC DEPLOYMENT AND METHODS OF MANUFACTURING SAME

FIELD OF THE INVENTION

The invention relates generally to a stent delivery system for placement of a stent in a body lumen, and more particularly to a stent delivery system for dynamic deployment of a stent within the body lumen.

BACKGROUND OF THE INVENTION

A wide range of medical treatments exist that utilize "endoluminal prostheses." As used herein, endoluminal prostheses is intended to cover medical devices that are adapted for temporary or permanent implantation within a body lumen, including both naturally occurring and artificially-made lumens, such as without limitation, arteries or veins, whether located within the coronary, mesentery, peripheral, or cerebral vasculature, gastrointestinal tract, biliary tract, urethra, trachea, hepatic shunts, and fallopian tubes.

Accordingly, a wide assortment of endoluminal prostheses have been developed, each providing a uniquely beneficial structure to modify the mechanics of the targeted lumen wall. For example, stents are hollow, generally cylindrical devices that are known for implantation within body lumens to provide artificial radial support to wall tissue that forms the various lumens within the body, and often more specifically, for implantation within blood vessels of the body. Stents may function to hold open and/or expand a segment of the blood vessel, and are often used in the treatment of atherosclerosis in blood vessels. One method for treating atherosclerosis and other forms of vessel narrowing is percutaneous transluminal angioplasty, commonly referred to as "angioplasty," "PTA" or "PTCA" when used in coronary arteries. The objective in angioplasty is to enlarge the lumen of the affected coronary artery by radial hydraulic expansion. The procedure is accomplished by inflating a balloon of a balloon catheter within the narrowed lumen of the coronary artery. In order to prolong the positive effects of PTCA and to provide radial support to the treated vessel, a stent may be implanted/deployed in conjunction with the procedure. Effectively, the stent overcomes the natural tendency of the vessel walls of some patients to close back down ("restenosis"), thereby maintaining a more normal flow of blood through that vessel than would be possible if the stent were not in place. A plastically deformable stent can be implanted during an angioplasty procedure by using a balloon catheter having a compressed or "crimped" stent loaded onto the balloon. The stent radially expands as the balloon is inflated, forcing the stent into contact with the body lumen, thereby forming a support for the vessel wall.

Deployment is effected after the stent has been percutaneously introduced and transluminally transported to be positioned at a desired location by means of the balloon catheter. Access to a treatment site is most often reached from the femoral artery. For treatment sites in small vessels that are remote from the insertion site, a flexible guiding catheter is inserted through an introducer sheath into the femoral artery. The guiding catheter is advanced through the vasculature to a treatment site, which may include advancement through the iliac artery, the ascending aorta and the aortic arch if the guiding catheter is to gain access to either the left or the right coronary artery, as desired. The procedure requires implantation of the stent, which has been loaded onto the balloon catheter, at a site remote from the insertion site, which means the stent is also guided through the potentially tortuous conduit of the vasculature to the treatment site. Therefore, the stent must be able to satisfy a number of mechanical requirements. First, the stent must possess sufficient flexibility to allow for crimping, expansion, and cyclic loading induced by the beating heart. Longitudinal flexibility is important to allow the stent to be maneuvered through a tortuous vascular path and to enable it to conform to a deployment site that may not be linear or may be subject to flexure. Second, the stent must be capable of withstanding the structural loads, namely radial compressive forces, imposed on the stent as it supports the walls of the vessel in which it is implanted. Therefore, a stent must possess adequate radial strength to maintain its size and shape throughout its service life despite the various forces that may come to bear on it, including the cyclic loading. For example, a radially directed force may tend to cause a stent to recoil inward, which is undesirable. Radial strength, which is the ability of a stent to resist radial compressive forces, is due to strength and rigidity around a circumferential direction of the stent. Radial strength and rigidity, therefore, may also be described as, hoop or circumferential strength and rigidity.

The structure of a stent is typically composed of scaffolding that includes a pattern or network of interconnecting structural elements often referred to in the art as struts. The scaffolding can be formed from wires, tubes, or sheets of material rolled into a cylindrical shape. The scaffolding is designed so that the stent has both flexibility, so as to be radially crimped onto the balloon catheter and advanced therewith through the vasculature, and radial strength, so as to be strong enough to provide radial support to the treatment site after implantation. Although there are innumerable stent designs that attempt to balance the competing requirements of flexibility and radial strength for use with stent delivery catheters, a need remains in the art for a stent delivery system that provides for deliverability and deployment of a stent such that the stent has a desirable balance of flexibility and radial strength.

BRIEF SUMMARY OF THE INVENTION

Embodiments hereof are directed to a stent delivery system for dynamic deployment of a stent loaded thereon and to a method of manufacturing the system. The stent delivery system includes a balloon catheter with an uninflated balloon in a spirally twisted delivery configuration on which a balloon-expandable stent is crimped or otherwise loaded. The stent is made from a single, continuous strand of wire formed into a sinusoidal waveform that is wrapped into a helical pattern and joined at selected crowns. Upon inflation of the spirally twisted balloon of the stent delivery system, the stent undergoes dynamic deployment such that the stent in a deployed or expanded configuration has crowns with obtuse deployment angles and crowns with acute deployment angles.

A method of manufacturing a stent delivery system for dynamic deployment of a stent in accordance herewith includes twisting an uninflated balloon of a stent delivery catheter into a spirally twisted delivery configuration and loading a stent onto the spirally twisted balloon, wherein the balloon-expandable stent is made from a single, continuous strand of wire formed into a sinusoidal waveform that is wrapped into a helical pattern and joined at selected crowns. The balloon and stent being configured such that upon inflation of the spirally twisted balloon the stent undergoes dynamic deployment with selected crowns of the deployed stent having obtuse deployment angles and other crowns of the deployed stent having acute deployment angles.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2CC is an enlarged view of an Area C of the stent of FIG. 2C.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
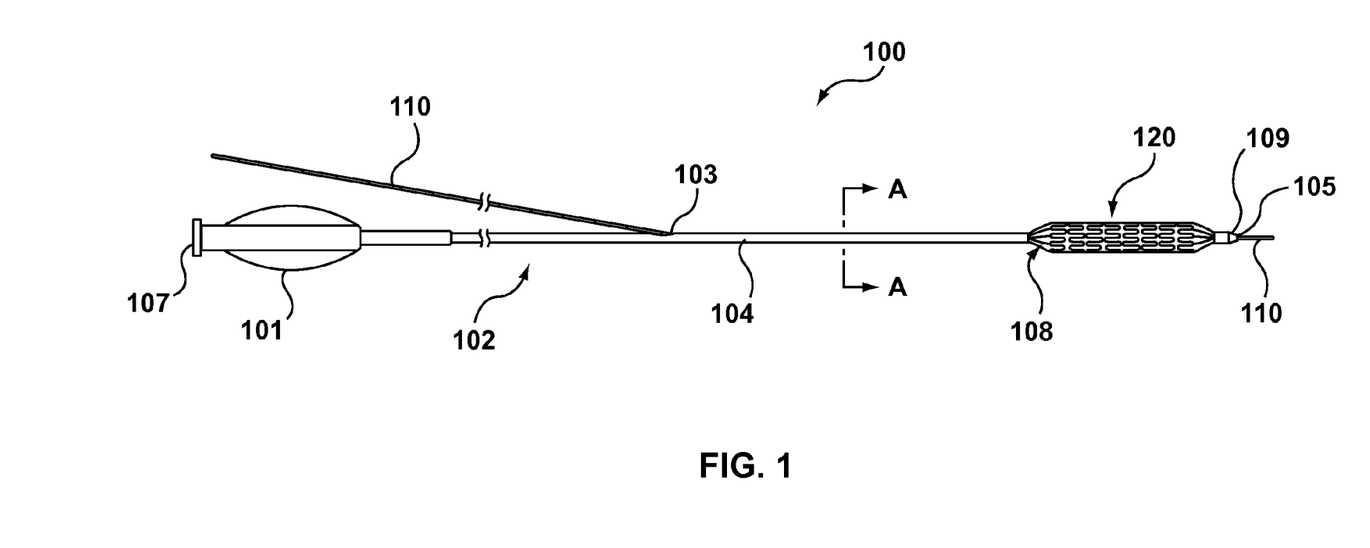
FIG. 1 is a side view of a stent delivery system in accordance with an embodiment hereof.
Figure 1A:
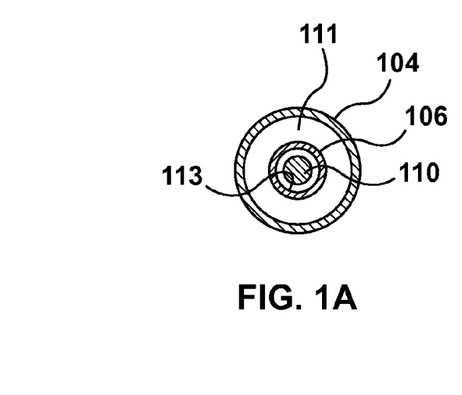
FIG. 1A is a transverse cross-sectional view of the stent delivery system shown in FIG. 1 taken along line A-A thereof.

FIG. 1 is a side view of a stent delivery system 100 in accordance with an embodiment hereof, with FIG. 1A being a transverse cross-sectional view taken along line A-A in FIG. 1. Stent delivery system 100 includes a balloon catheter 102 having an elongate shaft 104, a guidewire shaft 106 for slidably receiving a guidewire 110 through a guidewire lumen 113 thereof, and a balloon 108. Shaft component 104 has a proximal end attached to a hub 101 and a distal end attached to a proximal end of balloon 108. Guidewire shaft 106 extends within a distal portion of shaft component 104 and through balloon 108 from a side port 103 of shaft 104 to a distal tip 109, such that balloon catheter 102 has a rapid-exchange configuration. Distal tip 109 defines a distal port 105 through which guidewire 110 slidably extends. Hub 101 includes an inflation port 107, which may be a Luer fitting, for coupling to a source of inflation fluid. Inflation port 107 fluidly communicates with balloon 108 via an inflation lumen 111 that extends through shaft component 104. As would be understood by one of ordinary skill in the art in another embodiment, the guidewire shaft may extend the entire length of the balloon catheter between the hub and the distal tip of the catheter in an over-the-wire configuration. In such an embodiment, the hub may include a guidewire port that communicates with the guidewire lumen of the guidewire shaft for receiving a guidewire, such as guidewire 110, therethrough. In addition although in the cross-sectional view shown in FIG. 1A the guidewire shaft 106 and shaft component 104 are shown as concentrically disposed, this is by way of illustration only and other arrangements as would be understood by one of ordinary skill in the art are within the scope of the invention. In accordance with embodiments hereof, any known balloon catheters intended for angioplasty or stent delivery may be adapted for use in stent delivery system 100.

Figure 1B:
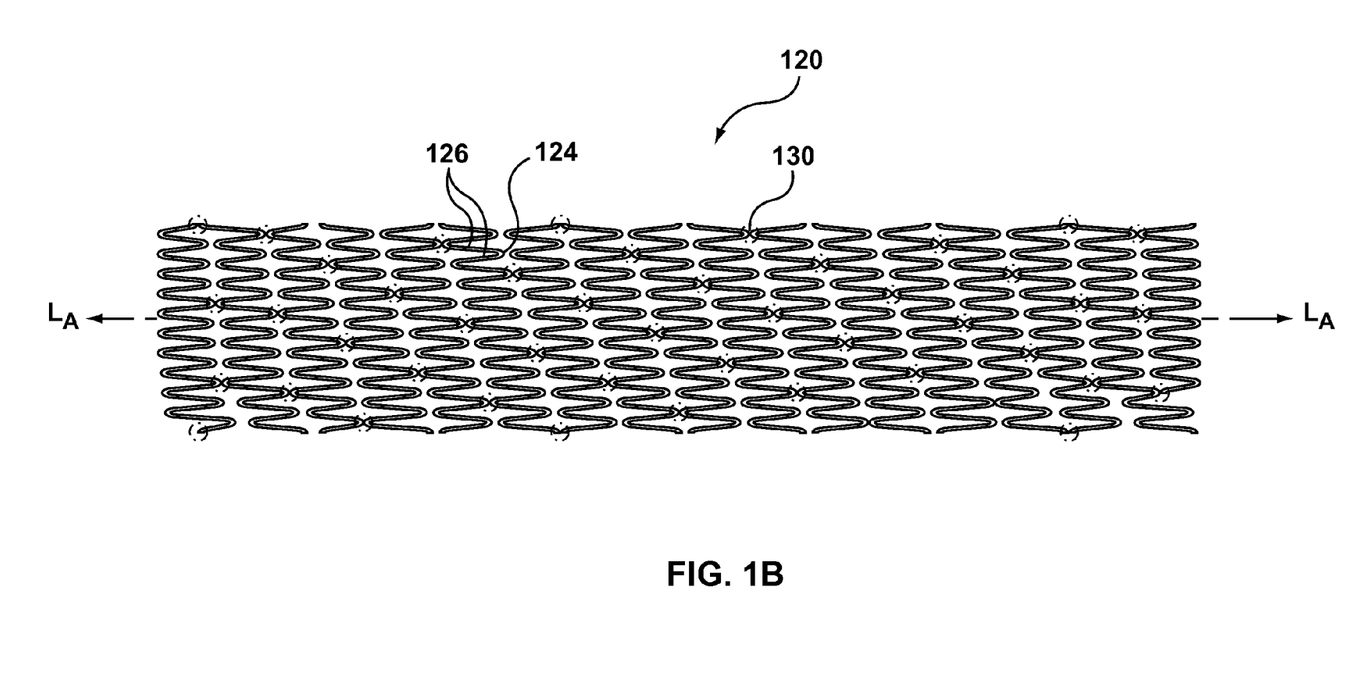
FIG. 1B is a side view of a stent removed from the stent delivery system of FIG. 1 and shown with its crimped, delivery configuration cut longitudinally and laid open for illustrative purposes only.

In FIG. 1 a balloon-expandable stent 120 of stent delivery system 100 is shown positioned over and crimped onto balloon 108 for delivery to a treatment site. FIG. 1B depicts stent 120 in its crimped, delivery configuration removed from stent delivery system 100, cut longitudinally and laid open for illustrative purposes only. In accordance with an embodiment hereof and with reference to FIG. 2A, stent 120 is formed of a single, continuous strand of wire 121 that has been formed into a sinusoidal waveform 122 having uniform crowns or bends 124 between adjacent struts 126. Stated another way, each crown 124 may be described as a curved portion or turn within waveform 122 that connects adjacent struts 126 to define the continuous sinusoidal waveform 122. In an embodiment, an apparatus for forming a continuous sinusoidal waveform as disclosed in U.S. Pat. Appl. Pub. No. 2013/0025339 to Costa et al., which is incorporated by reference herein in its entirety, may be used to create waveform 122. In embodiments hereof crowns 124 of waveform 122 are uniform in size and shape, such that crowns 124 of the helically wrapped stent 120 formed thereby are also uniform in size and shape when stent 120 is in its natural, formed (e.g. wrapped and welded) configuration shown longitudinally cut open and laid flat in FIG. 2C and when stent 120 is in its crimped, delivery configuration shown in FIG. 1B.

Figure 2:
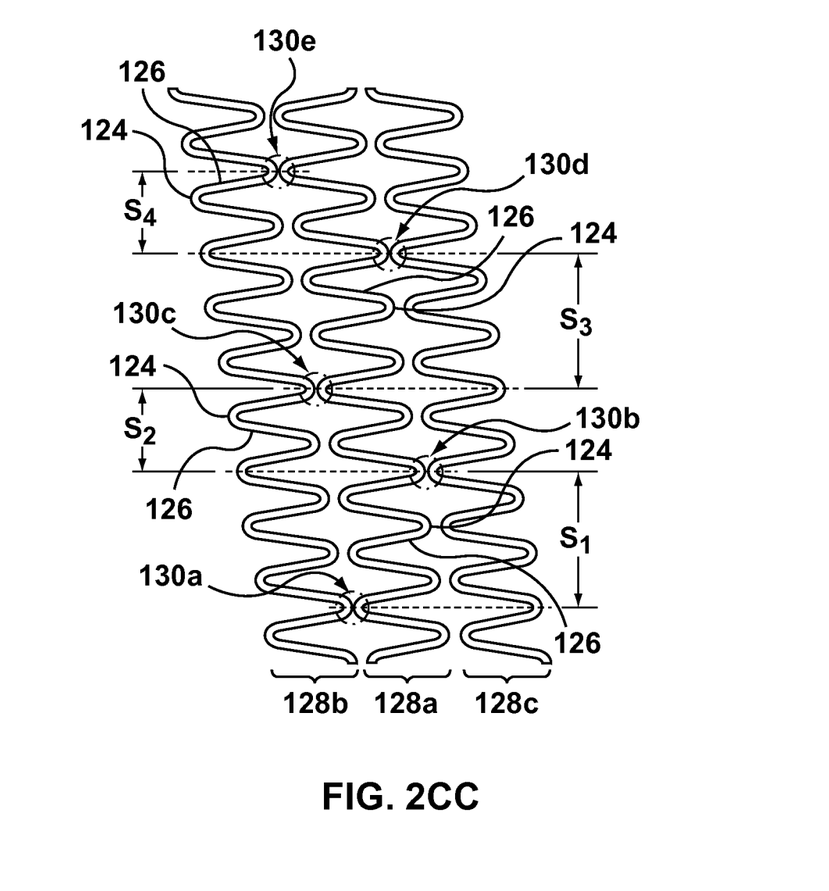
Figure 2A:
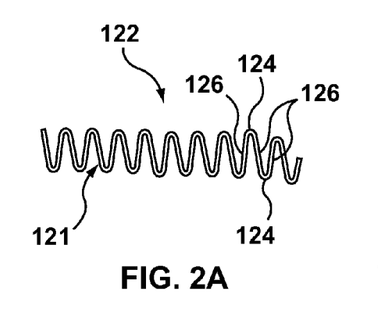
FIG. 2A depicts a portion of a waveform for forming a stent in accordance with an embodiment hereof.
Figure 2B:
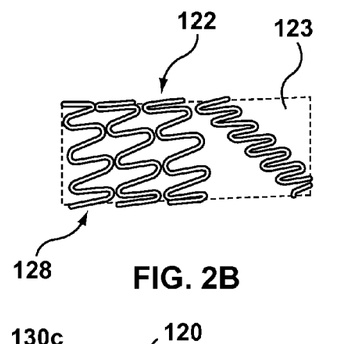
FIG. 2B depicts the waveform of FIG. 2A being wrapped to form a stent in accordance with an embodiment hereof.

In order to form stent 120, sinusoidal waveform 122 is wrapped in a helical pattern about a mandrel, rod or other forming device 123 as shown in FIG. 2B to form one of a right-handed or left-handed helix. With additional reference to FIG. 2C, each complete wrap of the waveform 122 around the mandrel 123 may be described as a turn 128 that is made at a helical angle A with respect to the longitudinal axis $L_A$ of stent 120 such that a plurality of adjacent turns 128 form the cylindrical or tubular shape of stent 120. It would be understood by one of ordinary skill in the art that the number of turns 128 and the helical angle A may be determined by particular specifications of the stent 120, such as the desired unexpanded and expanded diameters, and/or overall length of the stent, and/or a size (e.g., diameter) and particular material of wire 121 used to form the stent, and accordingly the illustrated embodiment is not intended to be limiting in any way. As well although stent 120 is depicted as being wrapped to form a right-handed helix in FIG. 2C, in other embodiments stent 120 may be wrapped to form a left-handed helix without departing from the scope hereof.

Figure 2C:
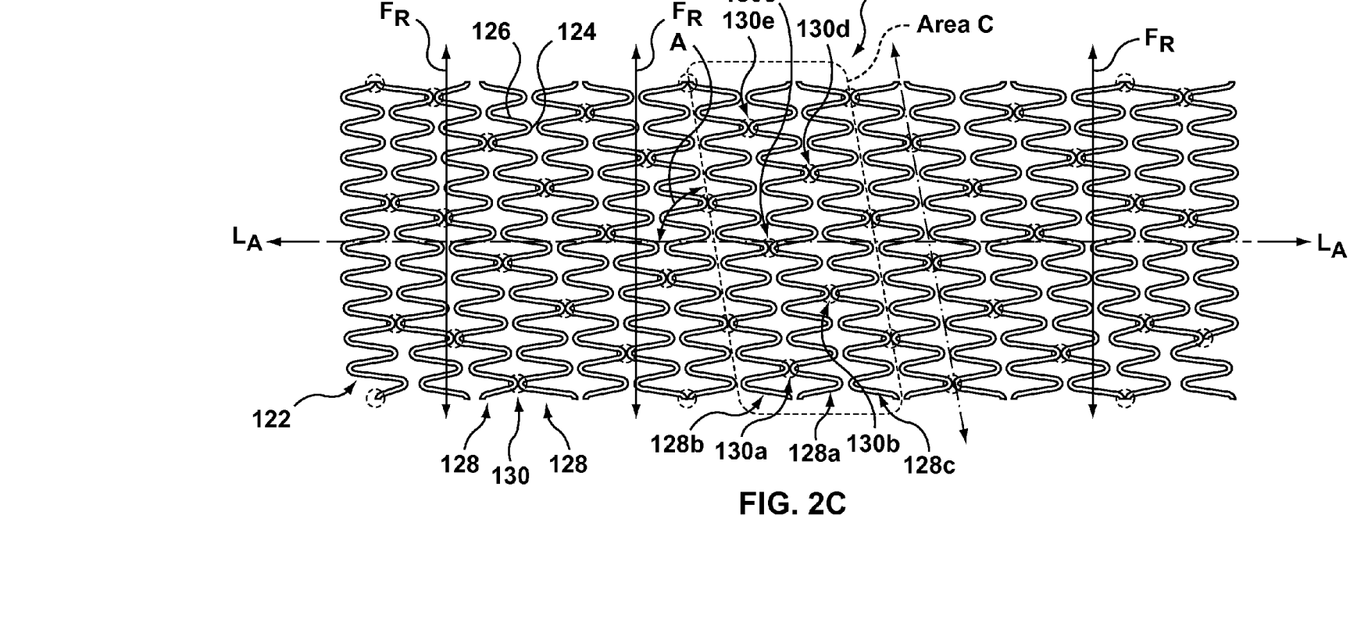
FIG. 2C is a side view of the stent of FIG. 1B shown with its natural, formed configuration cut longitudinally and laid open for illustrative purposes only.

Each turn 128 of the helically wrapped waveform 122 of stent 120 is connected to an adjacent turn 128 by one or more connections 130 that are configured to connect selected crowns 124 of adjacent turns 128. In FIGS. 1B, 2C, 2CC, and 5 hereof, connections 130 are denoted by dashed circles for illustrative purposes only. Specific locations for connections 130 are selected to ensure stent 120 has maximum flexibility and conformability. In the embodiment illustrated in FIG. 2C and with further reference to FIG. 2CC, a first connection 130a joins a crown of a turn 128a to a corresponding crown of an adjacent turn 128b and a second connection 130b along waveform 122 is made to join a crown of turn 128a to a corresponding crown of an adjacent turn 128c, wherein the adjacent turn 128c is on an opposite side of turn 128a from the adjacent turn 128b. With reference to FIG. 2CC that is an enlarged view of an Area C of FIG. 2C, a first segment $S_1$ of turn 128a of waveform 122 that extends between the two connections 130a, 130b includes five struts 126 and four unconnected or free crowns 124. A third connection 130c is the next connection made along the turn 128a and joins a crown of turn 128a with a corresponding crown of adjacent turn 128b. Third connection 130c is positioned along waveform 122 such that a second segment $S_2$ of turn 128a of waveform 122 that extends in between the two consecutive connections 130b, 130c includes three struts 126 and two free crowns 124. A fourth connection 130d is the next connection made along the turn 128a and joins a crown of turn 128a with a corresponding crown of adjacent turn 128c. Fourth connection 130d is positioned such that a third segment $S_3$ of turn 128a of waveform 122 that extends in between the two consecutive connections 130c, 130d includes five struts 126 and four free crowns 124. A fifth connection 130e is the next connection made along the turn 128a and joins a crown of turn 128a with a corresponding crown of adjacent turn 128b. Fifth connection 130e is positioned along waveform 122 such that a fourth segment $S_4$ of turn 128a of waveform 122 that extends in between the two consecutive connections 130d, 130e includes three struts 126 and two free crowns 124. Accordingly, the first segment $S_1$ of waveform 122 that extends between consecutive connections 130a, 130b and the third segment $S_3$ of waveform 122 that extends between consecutive connections 130c, 130d are each of the same length, and the second segment $S_2$ of waveform 122 that extends between consecutive connections 130b, 130c and the fourth segment $S_4$ of waveform 122 that extends between consecutive connections 130d, 130e are each of the same length. As well a length of the first and third segments $S_1$, $S_3$, which may be referred to herein as long segments, is greater or longer than a length of the second and fourth segments $S_2$, $S_4$, which may be referred to herein as short segments.

The pattern of spacing consecutive connections 130 of stent 120 such that segments of the waveform that extend therebetween alternate between long segments, such as the first and third segments $S_1$, $S_3$, and short segments, such as the second and fourth segments $S_2$, $S_4$, repeats along helically wrapped waveform 122 for at least a portion of the length of stent 120. In the embodiment shown in FIG. 2C the pattern of spacing connections so as to create long and short segments repeats for substantially the entire length of the stent except for the endmost connections at the proximal and distal ends of the stent. The endmost connections of the stent of FIG. 2C are substantially evenly spaced about the circumference of each end so as to provide axial stability thereto, and the last few turns of the wrapped waveform 122 at each end of stent 120 include a transition of the wrapping angle from the acute helical angle A, discussed above, to a more transverse angle at the endmost turns of waveform 122 in order to provide stent 120 with substantially squared-off ends. In another embodiment, the spacing between consecutive connections may be made such that the long segments may have additional or fewer struts and crowns therebetween than that shown in the embodiment of FIG. 2C, as long as the spacing between consecutive connections for defining short segments therebetween includes fewer struts and crowns than the long segments.

In an embodiment, connections 130 may be created by welding or fusing the selected crowns 124 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion. In another embodiment, connections 130 may be created by brazing or soldering the selected crowns 124 together. As used herein, "brazing" and "soldering" are defined as heating an additional material that is separate from the selected crowns and applying the heated additional material to the selected crowns 124 so that when the additional material cools, the selected crowns 124 are brazed or soldered together.

Suitable materials for balloon-expandable stent 120 include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, vanadium, and carbon, as well as combinations, alloys, and/or laminations thereof. For example, stent 120 may be formed from an age hardenable nickel-cobalt-chromium-molybdenum alloy sold under the trade name MP35N, cobalt-chromium-nickel alloy sold under the trade name ELGILOY, chromium-nickel-tungsten-cobalt alloy sold under the trade name L-605, or palladium-silver alloy sold under the trade name ABI). In other embodiments, stent 120 may be formed from two or more materials that are laminated together, such as platinum or tantalum that is laminated with MP35N. Stent 120 may also be formed from a wire having concentric layers of different metals, alloys, or other materials.

Figure 3A:
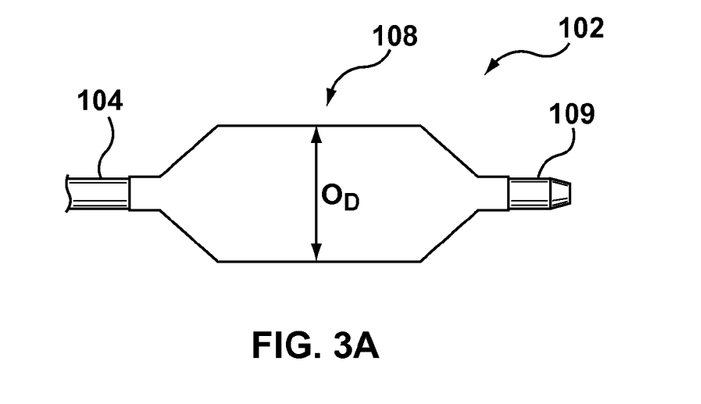
FIG. 3A is a side view of a balloon of the stent delivery system of FIG. 1 shown in an inflated or expanded configuration.
Figure 3B:
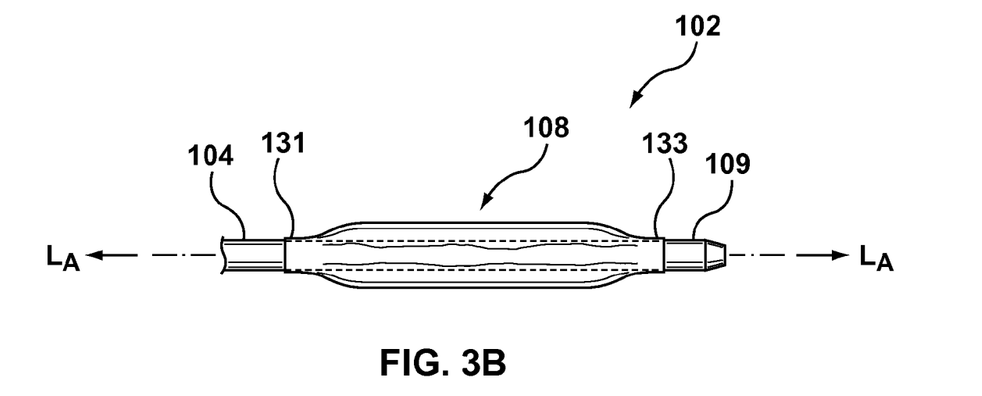
FIG. 3B is a side view of the balloon of FIG. 3A shown in an unexpanded configuration.
Figure 3C:
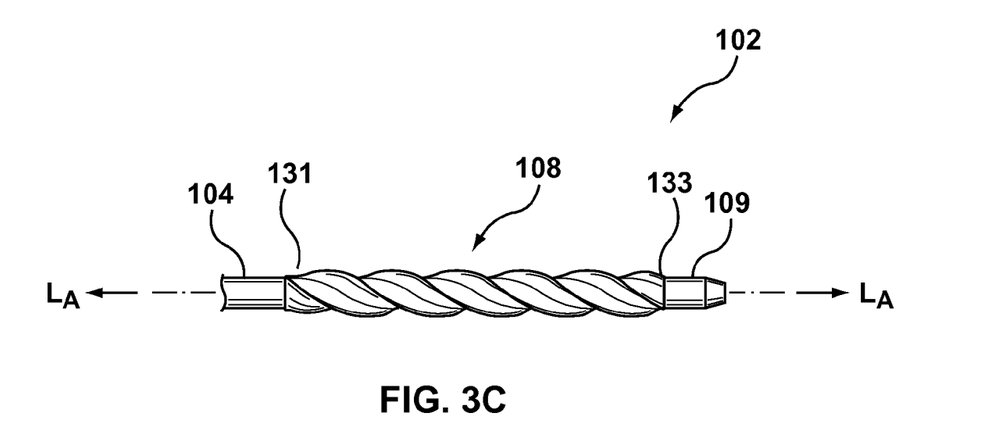
FIG. 3C is a side view of the balloon of FIG. 3B shown in a spirally twisted delivery configuration in accordance with an embodiment hereof.

In FIG. 2C stent 120 is depicted longitudinally cut open and laid flat in its natural, formed (e.g. wrapped and welded) configuration prior to being loaded or otherwise crimped, as shown in FIGS. 1 and 1B, onto balloon 108 of balloon catheter 102. In FIGS. 3A, 3B and 3C balloon 108 is shown without stent 120. Balloon 108 is depicted in an inflated configuration in FIG. 3A, in an uninflated, untwisted configuration in FIG. 3B, and in an uninflated, spirally twisted delivery configuration in FIG. 3C. Balloon 108 is a dilatation-type catheter balloon of a non-compliant material that is formed to have a certain or specific outer or working diameter $O_D$ when inflated, as shown in FIG. 3A. In accordance with embodiments hereof, balloon 108 may be made from a thermoplastic material or a thermoplastic elastomer, such as various polyesters and their block co-polymers, polyamides and their block co-polymers, and polyurethane block co-polymers. Dilatation balloon 108 according to various embodiments of the present invention may be made, for example, from materials and by methods disclosed in U.S. Pat. Nos. 5,500,180, 6,210,364, 6,283,939 to Anderson et al., and U.S. Patent Appl. Publ. No. 2006/0134357 to Godaire et al., each of which is incorporated by reference herein in its entirety.

Figure 4:
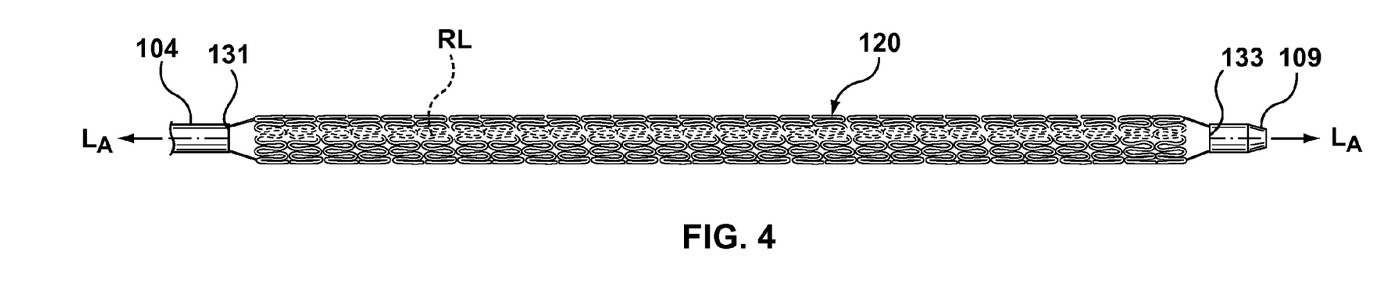
FIG. 4 is an enlarged side view of a distal portion of the balloon catheter of the stent delivery system of FIG. 1 with the stent in its crimped, delivery configuration loaded thereon.

In order to provide dynamic deployment of stent 120, balloon 108 in the uninflated configuration shown in FIG. 3B is twisted, wound, or otherwise turned about the longitudinal axis $L_A$ of catheter 102 in order to configure balloon 108 in the spirally twisted delivery configuration shown in FIG. 3C. The twisting of balloon 108 may be performed manually, by machine or by some combination of both manual and machine manipulation. For instance, when manually performed, balloon 108 may be twisted by holding shaft component 104 at proximal end 131 of balloon 108 in one hand while gripping and turning the adjacent part of balloon 108 around the longitudinal axis $L_A$ with the other hand, and thereafter distally advancing the twisting by moving both the twisting and grasping hands incrementally along balloon 108 to distal end 133 thereof. Once balloon 108 has been sufficiently twisted from substantially the proximal end 131 to the distal end 133 thereof, balloon 108 may be held under vacuum in the spirally twisted delivery configuration shown in FIG. 3C while stent 120 is positioned over and crimped thereon as shown in FIG. 4. In another example, a balloon folding machine may be used to soften areas of balloon 108 where desired pleats would locate in order to create a spiral or twisted pattern in the uninflated balloon, a negative pressure would then be applied to compress balloon 108 to an uninflated diameter, and the compressed balloon would be cured with a heat-treatment to set the spirally, twisted pattern of the balloon. Balloon 108 as shown in the spirally twisted delivery configuration of FIG. 3C may be described as having a spirally wrapped or twisted shape, as being comprised of twists, windings and/or turns of a material of the balloon, and/or as being twisted, wound or turned about the longitudinal axis $L_A$ of balloon catheter 102. In embodiments hereof, balloon 108 may be incrementally twisted in a clockwise direction from proximal end 131 to distal end 133 to form a right-handed helix or spiral, as shown in FIG. 3C, or alternatively may be incrementally twisted in a counterclockwise direction from proximal end 131 to distal end 133 to form a left-handed helix or spiral (not shown). In embodiments in accordance herewith, the direction of the twisting of the balloon and the right-handed or left-handed spiral formed thereby correlates with or matches the left-handed or right-handed helix or helical pattern of the stent that is loaded thereon and dynamically deployed thereby.

Figure 4A:
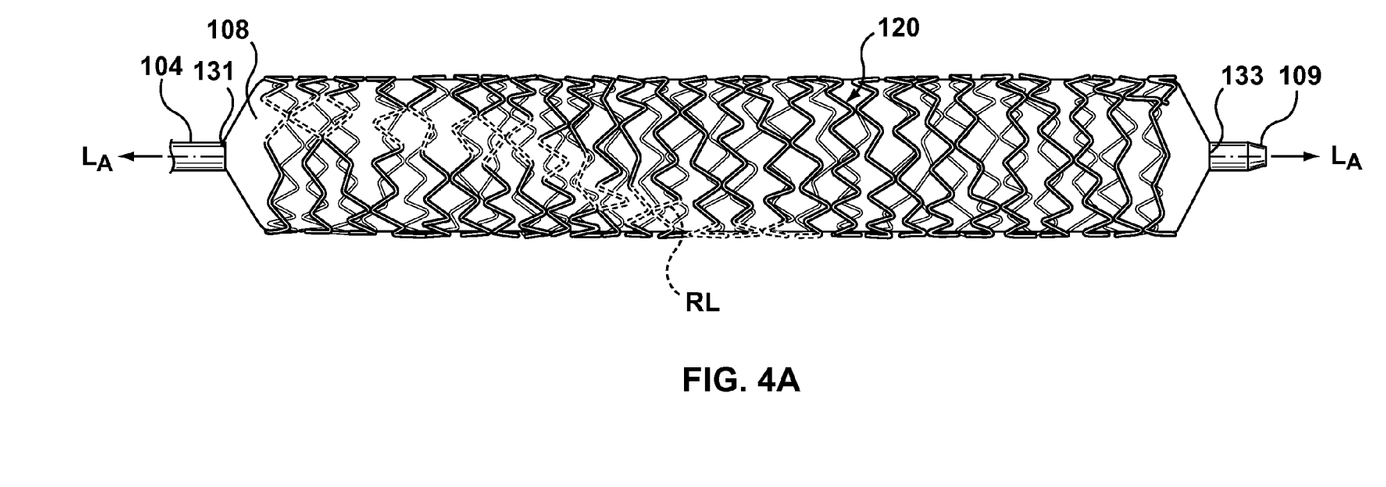
FIG. 4A is a side view of the distal portion of the balloon catheter shown in FIG. 4 with the stent of FIG. 2C dynamically deployed thereon in accordance with an embodiment hereof.

A conventionally folded, i.e. untwisted balloon radially expands to provide substantially uniform radial expansion of a stent crimped thereon. If stent 120 formed in accordance with an embodiment hereof was crimped onto and expanded by a conventionally folded balloon of a balloon catheter, the radial expansion force of the balloon as depicted by lines $F_R$ in FIG. 2C would cause substantially uniform radial expansion of stent 120 such that crowns of the deployed stent would undergo substantially the same amount of radial expansion and thereby have substantially uniform deployment angles. In contrast, spirally twisted balloon 108 in accordance with an embodiment hereof untwists or otherwise unwinds as it is inflated and thereby provides an expansion force that torques or twists stent 120 to provide dynamic deployment thereof, as shown in FIG. 4A. In other words, the untwisting of balloon 108 during inflation applies a twisting force to stent 120 as it radially expands the stent that results in the dynamic deployment of the stent. To illustrate a direction of at least a component of the expansion force experienced by stent 120 by the untwisting of balloon 108 during inflation, a broken reference line RL that is parallel with the longitudinal axis $L_A$ of the stent is drawn on crimped stent 120 in FIG. 4. In FIG. 4A the stent 120 is shown after dynamic deployment, wherein broken reference line RL is no longer parallel with the longitudinal axis $L_A$ of stent 120 in FIG. 4A, but instead at least partially wraps about the longitudinal axis $L_A$ of the stent, which occurs due to the twisting force experienced by stent 120 during the inflation of spirally twisted balloon 108. A comparison of reference line RL as it appears in FIGS. 4 and 4A, thus illustrates that the untwisting of balloon 108 during expansion is configured to torque or otherwise twist stent 120 to provide the dynamic deployment thereof.

Figure 5:
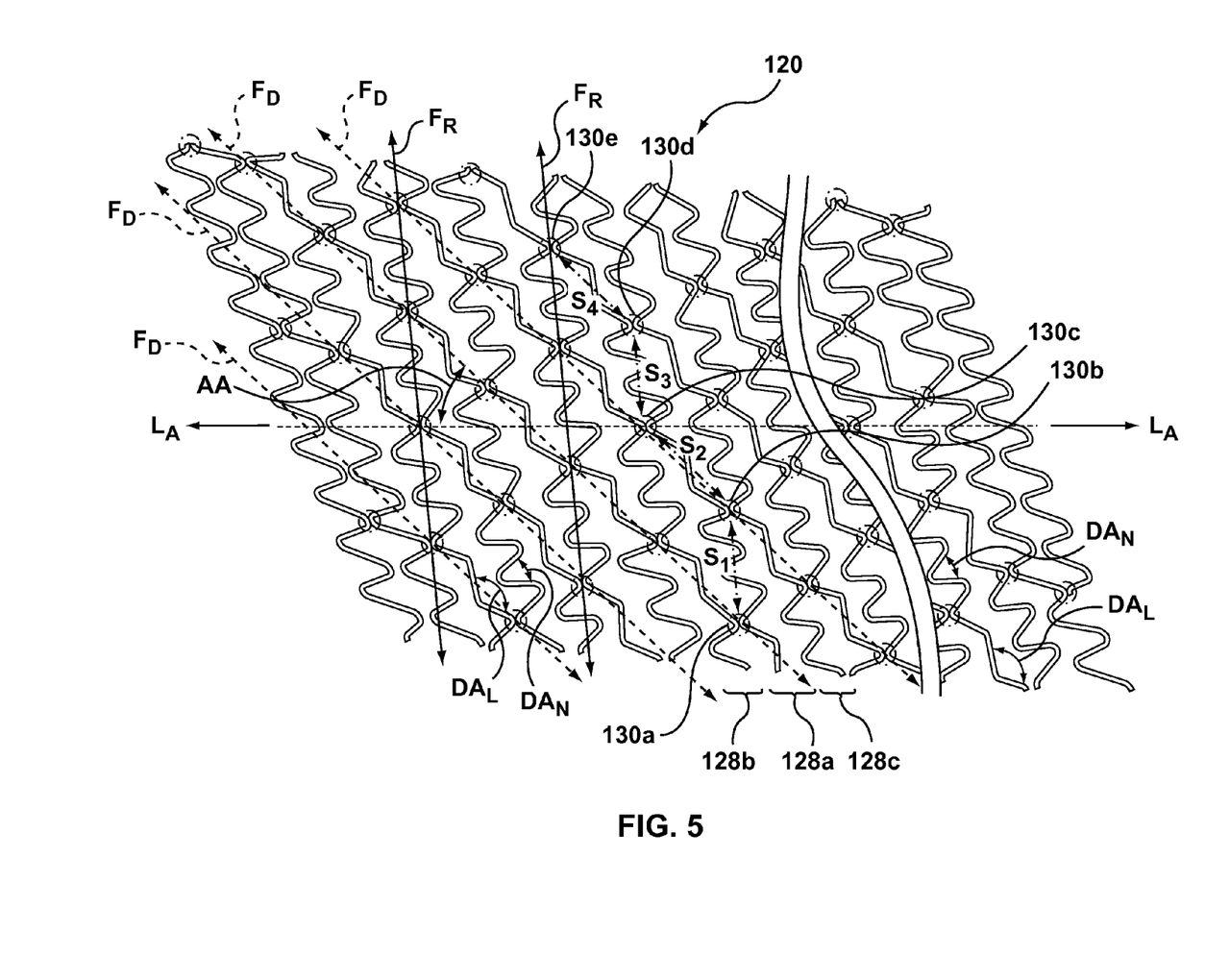
FIG. 5 depicts the dynamically deployed stent of FIG. 4A in accordance with an embodiment hereof cut longitudinally and laid open for illustrative purposes only.

With reference to FIG. 5 that depicts dynamically deployed stent 120 removed from balloon 108, cut longitudinally and laid open for illustrative purposes only, diagonal lines $F_D$ represent forces acting on stent 120 due to the torque applied by the untwisting of balloon 108 during expansion. Diagonal lines $F_D$ are at an acute angle AA with respect to the longitudinal axis $L_A$ of stent 120, and the forces represented thereby are believed to provide the dynamic deployment of stent 120. The term "dynamic deployment" is meant to convey that the expansion force provided by the untwisting or unwinding of balloon 108 preferentially stretches selected segments of stent 120 such that crowns within the selected segments have large deployment angles $DA_L$ as compared to crowns that lie within other segments of stent 120, which may be described as having relatively smaller, nominal or conventional deployment angles $DA_N$. In other words, unlike a stent expanded by a conventionally folded balloon in which each crown of the stent would undergo the same amount of radial expansion such that the crowns attain substantially uniform deployment angles, stent 120 undergoes dynamic deployment during the untwisting of balloon 108 such that, after expansion, selected segments of the stent have crowns with large deployment angles and other segments of the stent have crowns with nominal deployment angles. In an embodiment, the large deployment angles $DA_L$ achieved by dynamic deployment of stent 120 have an obtuse angle in the range of greater than 90 ninety degrees to less than or equal to 180 degrees, whereas the crowns with smaller, nominal or conventional deployment angles $DA_N$ have an acute angle in the range of greater than or equal to 70 degrees to less than 90 degrees.

With reference to FIGS. 2C, 2CC and 5, selected segments of stent 120 having crowns with large deployment angles are short segments of waveform 122 defined between two consecutive connections, such as second and fourth segments S2, S4 of turn 128a. In contrast, segments of stent 120 having crowns with shorter, nominal deployment angles are long segments of waveform 122 defined between two consecutive connections, such as first and third segments S1, S3 of turn 128a. The short segments of the waveform of stent 120 having crowns with large deployment angles align with or fall along diagonal lines FD in FIG. 5 and one or more aligned short segments form a section or sections of stent 120 that have high hoop strength for providing radial strength and stiffness to the deployed stent. In an embodiment, after expansion short segments of the helically wrapped waveform having crowns with large deployment angles may be described as having been substantially straightened from their pre-deployment sinusoidal waveform. The long segments of the waveform of stent 120 having crowns with nominal deployment angles align with or fall along radial lines FR in FIG. 5 and one or more aligned long segments form a section or sections of stent 120 that have flexibility and sufficient scaffolding for apposition with the vessel wall. In an embodiment, after expansion long segments of the helically wrapped waveform having crowns with nominal or conventional deployment angles may be described as having retained a sinusoidal waveform after expansion.

Due to the dynamic deployment provided by stent delivery system 100, stent 120 has a desirable balance of flexibility and radial strength. In comparison to a similarly constructed stent that is delivered without dynamic deployment of the present invention, in embodiments hereof stent 120 may be formed with fewer crowns per wrap/turn and with thinner strut widths to have a smaller or lower crossing profile without sacrificing radial strength when dynamically deployed. Accordingly, a stent formed in accordance with embodiments hereof utilizes dynamic deployment to control deployment angles for each crown such that selective crowns deploy to large deployment angles to increase radial strength while the remaining crowns deploy to nominal deployment angles to retain sufficient scaffolding and flexibility/conformability.

Stents of the present invention may be formed using any of a number of different methods. For example, the stents may be formed by winding a wire or ribbon around a mandrel to form the pattern described above and then welding or otherwise mechanically connecting two ends thereof to form bands. The bands are subsequently connected together to form the stent body. Alternatively, stents may be manufactured by machining tubing or solid stock material into toroid bands or rings, and then bending the bands on a mandrel to form the zig-zag pattern described above. Selected crowns of the bands formed in this manner are subsequently connected together to form the longitudinal stent body. Laser or chemical etching or another method of cutting a desired shape out of a solid stock material or tubing may also be used to form stents of the present invention. Further, a stent of the present invention may be manufactured in any other method that would be apparent to one skilled in the art. The cross-sectional shape of the struts of the finished stent may be circular, ellipsoidal, rectangular, hexagonal rectangular, square, or other polygon, although at present it is believed that circular or ellipsoidal may be preferable.

In embodiments hereof, an elongate shaft or tubular component for use as shaft 104 or guidewire shaft 106 of balloon catheter 102 and/or portions or layers thereof may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. In other embodiments for use as shaft 104 in accordance herewith, an elongate shaft or tubular component may be comprised of a proximal portion formed from a hypotube of a medical grade stainless steel with a distal portion thereof being formed from any of the polymeric materials listed above.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of manufacturing a stent delivery system for dynamic deployment of a stent comprising: twisting an uninflated balloon of a stent delivery catheter into a spirally twisted delivery configuration; and
    loading a stent onto the spirally twisted balloon, the stent being made from a single, continuous strand of wire formed into a sinusoidal waveform that defines crowns and struts of the stent, the sinusoidal waveform having been wrapped into a helical pattern and joined at selected crowns to form the stent,
    inflating the balloon, wherein the spirally twisted balloon untwists upon inflation and thereby applies a twisting force to the stent such that the stent undergoes dynamic deployment, and
    wherein the stent in a deployed configuration after dynamic deployment has crowns with obtuse deployment angles and crowns with acute deployment angles.

2. The method of claim 1, wherein the acute deployment angles are in the range of greater than or equal to 70 degrees to less than 90 degrees.

3. The method of claim 1, wherein in the deployed configuration one or more segments of the stent having crowns with obtuse deployment angles possess a higher hoop strength than one or more segments of the stent having crowns with acute deployment angles.

4. The method of claim 1, wherein the step of loading includes crimping the stent into a delivery configuration on the spirally twisted balloon.

5. The method of claim 4, wherein in the delivery configuration crowns of the stent are uniform in shape.

6. The method of claim 1, wherein the step of twisting the balloon includes incrementally twisting the balloon in a clockwise direction from a proximal end to a distal end thereof such that the spirally twisted balloon has a right-handed spiral and wherein the helical pattern of the stent forms a right-handed helix.

7. The method of claim 1, wherein the step of twisting the balloon includes incrementally twisting the balloon in a counterclockwise direction from a proximal end to a distal end thereof such that the spirally twisted balloon has a left-handed spiral and wherein the helical pattern of the stent forms a left-handed helix.

8. The method of claim 1, wherein the selected crowns of the sinusoidal waveform are joined to define alternating long and short segments between consecutive joined crowns of the stent and wherein after the stent undergoes dynamic deployment the short segments have free crowns with obtuse deployment angles and the long segments have free crowns with acute deployment angles.

9. The method of claim 8, wherein the long segments include more struts and free crowns than the short segments.

10. The method of claim 8, wherein after the stent undergoes dynamic deployment one or more of the short segments having free crowns with obtuse deployment angles align with a diagonal line that is at an acute angle relative to a longitudinal axis of the stent.

11. A method of manufacturing a stent delivery system for dynamic deployment of a stent comprising:
   twisting an uninflated balloon of a stent delivery catheter into a spirally twisted delivery configuration; and
   loading a stent onto the spirally twisted balloon, the stent being made from a single, continuous strand of wire formed into a sinusoidal waveform that defines crowns and struts of the stent, the sinusoidal waveform having been wrapped into a helical pattern and joined at selected crowns to form the stent, wherein the step of twisting the balloon provides the spirally twisted balloon with a right-handed spiral and wherein the helical pattern of the stent forms a right-handed helix,
   inflating the balloon, wherein the spirally twisted balloon untwists upon inflation and thereby applies a twisting force to the stent such that the stent undergoes dynamic deployment, and
   wherein the stent in a deployed configuration after dynamic deployment has crowns with obtuse deployment angles and crowns with acute deployment angles.

12. The method of claim 11, wherein the selected crowns of the sinusoidal waveform are joined to define alternating long and short segments between consecutive joined crowns of the stent and wherein after the stent undergoes dynamic deployment the short segments have free crowns with obtuse deployment angles and the long segments have free crowns with acute deployment angles.

13. The method of claim 12, wherein the long segments include more struts and free crowns than the short segments.

14. The method of claim 12, wherein after the stent undergoes dynamic deployment one or more of the short segments having free crowns with obtuse deployment angles align with a diagonal line that is at an acute angle relative to a longitudinal axis of the stent.

15. The method of claim 11, wherein the acute deployment angles are in the range of greater than or equal to 70 degrees to less than 90 degrees.

16. A method of manufacturing a stent delivery system for dynamic deployment of a stent comprising:
   twisting an uninflated balloon of a stent delivery catheter into a spirally twisted delivery configuration; and
   loading a stent onto the spirally twisted balloon, the stent being made from a single, continuous strand of wire formed into a sinusoidal waveform that defines crowns and struts of the stent, the sinusoidal waveform having been wrapped into a helical pattern and joined at selected crowns to form the stent, wherein the step of twisting the balloon provides the spirally twisted balloon with a left-handed spiral and wherein the helical pattern of the stent forms a left-handed helix,
   wherein the spirally twisted balloon is configured to untwist upon inflation and thereby apply a twisting force to the stent such that the stent undergoes dynamic deployment, and
   wherein the stent in a deployed configuration after dynamic deployment is configured to have crowns with obtuse deployment angles and crowns with acute deployment angles.

17. The method of claim 16, wherein the selected crowns of the sinusoidal waveform are joined to define alternating long and short segments between consecutive joined crowns of the stent and wherein after the stent undergoes dynamic deployment the short segments have free crowns with obtuse deployment angles and the long segments have free crowns with acute deployment angles.

18. The method of claim 17, wherein the long segments include more struts and free crowns than the short segments.

19. The method of claim 17, wherein after the stent undergoes dynamic deployment one or more of the short segments having free crowns with obtuse deployment angles align with a diagonal line that is at an acute angle relative to a longitudinal axis of the stent.

20. The method of claim 16, wherein the acute deployment angles are in the range of greater than or equal to 70 degrees to less than 90 degrees.

* * * * *